United States Patent
Rao et al.

(10) Patent No.: US 6,896,917 B2
(45) Date of Patent: May 24, 2005

(54) PROCESS FOR PREPARATION OF PROTEIN-HYDROLYSATE FROM SOY FLOUR

(75) Inventors: Appu Rao Gopala Rao Appu Rao, Mysore (IN); Hole Narasipura Nanjundaiah Chandrasekhara, Mysore (IN); Karadka Govindaraju, Mysore (IN); Johny Joseph, Mysore (IN); Kolara Subramanyam Krishna Murthy, Mysore (IN); Vishweshwariah Prakash, Mysore (IN); Mysore Cheeluvaraya Shamanthaka Sastry, Mysore (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 09/811,780

(22) Filed: Mar. 19, 2001

(65) Prior Publication Data

US 2002/0132028 A1 Sep. 19, 2002

(51) Int. Cl.[7] .............................. A23L 1/20; A23J 3/16; A23J 3/34

(52) U.S. Cl. ............................ 426/46; 426/52; 426/634
(58) Field of Search ............................ 426/46, 52, 656, 426/634, 640

(56) References Cited

U.S. PATENT DOCUMENTS

| | | | | |
|---|---|---|---|---|
| 3,753,728 A | * | 8/1973 | Bedenk et al. ................. | 426/44 |
| 3,876,806 A | * | 4/1975 | Hempenius .................... | 426/18 |
| 4,015,019 A | * | 3/1977 | Sawada et al. ................ | 426/46 |
| 4,757,007 A | * | 7/1988 | Satoh et al. .................. | 210/632 |
| 5,100,679 A | * | 3/1992 | Delrue .......................... | 426/44 |

* cited by examiner

*Primary Examiner*—Keith Hendricks
(74) *Attorney, Agent, or Firm*—Dickinson Wright PLLC

(57) ABSTRACT

A process for preparation of protein hydrolysate from soy flour. The process comprises the steps of hydrolyzing an aqueous slurry of defatted soy flour containing 6–30% solid content w/v using proteolytic enzyme of plant origin at a pH of 5-9 and at a temperature of 53±5° C. under stirring for 30 minutes to 6 hours; inactivating the enzyme by a known manner, neutralizing the pH value of the slurry, separating the solids by a known manner, and drying the clarified liquor so obtained to get the hydrolysate.

12 Claims, No Drawings

PROCESS FOR PREPARATION OF PROTEIN-HYDROLYSATE FROM SOY FLOUR

FIELD OF THE INVENTION

The present invention relates to a process for the preparation of protein hydrolysate from soy flour using a proteolytic enzyme of plant origin. Particularly, the present invention relates to a process for the preparation of protein hydrolysate from defatted soy flour using papain.

BACKGROUND OF THE INVENTION

Presently about 6.8 M tons of soybean is produced in India and extracted for oil. The solvent extracted flour is exported to foreign countries for feed purposes. By providing additional facilities for the hygienic processing of soybean in the solvent extraction units, it is possible to obtain edible grade defatted flour having the desired functional characteristics. After the recovery of oil, 4.9 M tons of soy flour is available in India for utilization. A small portion of the total soybean produced also finds its use for different edible grade flours, protein isolate and texturized products. The popularity of these products are greatly increasing worldwide. Soybean - which contains about 40% protein - is an excellent source this complex substance. New manufacturing techniques for high quality soybean foods have been developed by lowering or destroying the anti-nutritional factors such as trypsin inhibitors.

U.S. Pat. No. 5,180,597 discloses a process for hydrolyzed vegetable protein with enhanced flavor, which contains no detectable level of monochlorodihydroxypropanol. In the above reference, wheat gluten is hydrolyzed using Prozyme 6 (a fungal protease) at a temperature of 40–50° C., pH 6.5–7.0, enzyme concentration of 0.1–2% of substrate for a time period of 4 h. The hydrolyzed protein is treated with gaseous HCl for deamidation before the addition of acid for inactivating the enzyme. The drawback in such hydrolysis is that it is likely to lead to racemisation of amino acids and the addition of acid increases the salt content in the product.

U.S. Pat. No. 5,077,062 discloses a low sodium, low mono sodium glutamate soy hydrolysate that is prepared from soy material such as soy flour, soy meal or soy grits using fungal protease in water. The hydrolysis is conducted in the absence of acid or base at 90° C. for 2 h. After deactivating the enzyme and de-watering the mixture, the resulting hydrolysate contains between 45 and 55 wt. % enzymatically hydrolysed soy based protein with an average molecular weight of 670,000±50,000. The fungal protease used is different from the enzyme used in the present invention. The process is energy intensive due to the high temperature (90° C.) used.

U.S. Pat. No. 4,757,007 discloses the preparation of two hydrolyzed products using a protease from soy protein. The soy protein is hydrolyzed with papain or pepsin after precipitating with alcohol. The drawback of the process is that it involves the separation of the mixture of hydrolyzed products. Hydrolysis is carried out using papain or pepsin. Acidification is carried out to bring down the pH to 2.5–5.0 to separate the two kinds of hydrolysates, which could lead to an increase in salt content.

European Patent No. 0148600 B1 relates to the preparation of hydrolyzed protein from protein isolate after jet cooking or dynamic heating at 104° C. for a few seconds and later cooling in a vacuum chamber before performing hydrolysis using bromelin. The protein was precipitated at its isoelectric point from an aqueous extract of the material before the hydrolysis. The drawback of the process is that the starting material protein isolate is more expensive. The process is a multi-step process, and is energy intensive. The process further needs machines like the jet cooker and a vacuum chamber.

European Patent No. 0223560 A2 discloses a method describing the separation of protein hydrolysates with meat and cheese, favor from proteinaceous feed stocks (e.g. containing soybean, gluten, whey, casein, hemoglobin, yeast, cereal or microbial proteins) by stepwise hydrolysis using an endopeptidase followed by amino peptidase from *Streptococcus lactus*. The drawback of the process is that it is a multi-step process.

European Patent No. 0087246 B1 discloses a process for the hydrolysis of soybeans, wheat gluten and cotton seeds using fungal protease from Aspergillus and pancreatin (trypsin, chymotrypsin A, B and C, elastase and carboxypeptidase A and B). Activated charcoal is used to treat the hydrolysate, which is used for nutritional improvement. The drawback of the process is that it involves more steps.

European Patent No. 0187048 A2 describes the preparation of soy protein hydrolysate with 0.25 to 2.5% degree of hydrolysis (DH) using microbial rennet (*Mucor miehei*) and to be used as an egg white substitute. The enzyme used in the process is different and involves very low DH of soy protein.

United Kingdom Patent No. 2053228A describes a process for the production of soy protein hydrolysate from partially defatted soy material by hydrolysis with proteolytic enzyme. The drawback of the process is that due to the partial defatting soy flour, remaining oil comes in contact with the protein phase, which could lead to off-flavors.

U.S. Pat. No. 4,324,805 describes a method for producing soy protein hydrolysate and oil from partially defatted soy material by hydrolysis with a proteolytic enzyme. The soyflour is partially defatted by water washing at pH 3.5–4.5 and later hydrolyzed using water and a base to increase the pH. The DH is in the range of 8–12%. Oil is recovered from the wash water. Alcalase is the enzyme used. The drawback of the process is that it is a multi step process and due to partial defatting of soy flour, remaining oil comes in contact with the protein phase which could lead to off-flavors. Enzyme inactivation is done by the addition of acid, which is likely to lead to increased salt content in the product.

U.S. Pat. No. 3,640,725 describes an enzymatic hydrolysis process for the production of soy protein hydrolysates. The soy seeds are comminuted and heated at 90–140° C. Protease (fungal and bacterial) is added at 25–75° C. The fiber is separated and slurry has two phases - an oil and an aqueous phase. The aqueous phase is brought to pH 4.5 to precipitate the protein, which is then concentrated. The starting material is not defatted and hence the residual oil could come in contact with the aqueous phase, which could lead to off-flavors.

Canadian Patent No. 905742 describes a soy protein hydrolysate modified with pepsin to yield a product which, in the presence of water and sugar, whips at a rapid rate to produce aerated products of low density.

European Patent No. 0797928A1 describes a process for the manufacture of a soy protein hydrolysate with a protease used selectively to decompose glycinin at a pH of 1.5–2.5. The pH used in the process is very low and therefore differs from the pH used in the present invention. Further, the aim of the process is to achieve a low glycinin content which is not the case in the present invention.

Reference may be made to a published paper entitled "Industrial production and application of soluble enzymatic hydrolysate of soy protein" (Olsen, H. S., Adler Nissen, J., [1979], Process Biochemistry, 14[7], 6,8, 10–11), wherein a method for preparation of soy protein hydrolysate from soy flakes washed at pH 4.5 followed by hydrolysis using alcalase is described. The solubility of the substrate is low at the acidic pH which is likely to result in low yields. The enzyme used is different from the enzyme used in the present invention.

OBJECTS OF THE INVENTION

The main object of the present invention is to provide a process for the preparation of protein hydrolysate from soy flour from plant based protease.

Another object of the present invention is to provide a process for the preparation of protein hydrolysate with a specified degree of hydrolysis.

Still another object of the present invention is to provide a process for the preparation of protein hydrolysate soluble in water over a wide range of pH values.

Yet another object of the present invention is to provide a process for the preparation of protein hydrolysate which can be used for nutritional enrichment.

SUMMARY OF THE PRESENT INVENTION

The invention provides a process for the preparation of protein hydrolysate from soy flour, the process comprising the steps of: hydrolyzing an aqueous slurry of defatted soy flour containing 6–30% solid content w/v using proteolytic enzyme of plant origin at pH 5–9 and a temperature of 53±5° C. under stirring for 30 min to 6 h; inactivating the enzyme by a known manner; neutralizing the pH value of the slurry; separating the solids by a known manner and drying the clarified liquor so obtained to get the said hydrolysate.

DESCRIPTION OF THE INVENTION

Accordingly, the present invention provides a process for the preparation of protein hydrolysate from soy flour, the process comprising the steps of: hydrolyzing an aqueous slurry of defatted soy flour containing 6–30%, solid content w/v using proteolytic enzyme of plant origin at pH 5–9 and a temperature of 53±5° C. under stirring for 30 min to 6 h; inactivating the enzyme by a known manner; neutralizing the pH value of the slurry; separating the solids by a known manner and drying the clarified liquor so obtained to get the said hydrolysate.

In an embodiment of the present invention, the solid content of the slurry is 20% w/v.

In another embodiment of the present invention, the plant origin proteolytic enzyme is selected from the group comprising papain and bromelin.

In still another embodiment of the present invention, 0.4–0.6 w/w of the proteolytic enzyme is added to the soy flour.

In yet another embodiment of the present invention, the hydrolysis is effected for a period of 3–4 hours.

In one more embodiment of the present invention, they drying is effected by freeze drying, spray drying or drum drying.

In one other embodiment of the present invention, the protein hydrolysate produced has decreased bitterness.

In an embodiment of the present invention, the protein hydrolysate produced is less hygroscopic in nature.

In another embodiment of the present invention, the protein hydrolysate has 2–2.2 g/100 ml bitterness recognition threshold units.

In still another embodiment of the present invention, the protein hydrolysate produced has low mineral content.

In one more embodiment of the present invention, high yield of protein hydrolysate with 30 to 35% degree of hydrolysis is obtained from the selected raw material.

In one other embodiment of the present invention, a protein hydrolysate having creamy color and a yield of 20 to 25% (on flour basis) is obtained.

In a further embodiment of the present invention, the protein hydrolysate has 3.0 to 5.0% moisture, 8.0 to 8.5% nitrogen and 30.0–35.0% degree of hydrolysis.

In another embodiment of the present invention, the protein hydrolysate obtained has 25–30 trypsin inhibitor units/mg activity, 95 to 98% Nitrogen Solubility Index and 1.0 to 1.4% of salt content.

In still another embodiment of the present invention, lipoxygenase and urease activities of the protein hydrolysate are not detectable.

In yet another embodiment of the present invention, the amino acid composition of the protein hydrolysate is similar to the amino acid makeup as that of the starting material.

In one more embodiment of the present invention, the protein hydrolysate retained the nutrition value as in the starting material.

In one another embodiment of the present invention, the protein hydrolysate does not impart any undesirable flavor for the finished product.

In an embodiment of the present invention, the solubility of the protein hydrolysate is independent of the pH value.

The present invention also provides a protein hydrolysate creamy in color.

In still another embodiment of the present invention, the protein hydrolysate has 3 to 5% moisture, 8 to 8.5% nitrogen and 30 to 35% degree of hydrolysis.

In yet another embodiment of the present invention, the protein hydrolysate has 20 to 30 trypsin inhibitor units/mg activity, 95 to 98% Nitrogen Solubility Index and 1 to 1.4% of salt content.

In one more embodiment of the present invention, the protein hydrolysate has 2 to 2.2 g/100 ml bitterness recognition threshold.

In one another embodiment of the present invention, the lipoxygenase and urease activities of the protein hydrolysate are not detectable.

In an embodiment of the present invention, the amino acid composition of the protein hydrolysate is similar to the amino acid makeup of the starting material.

In another embodiment of the present invention, the protein hydrolysate retained the nutrition value present in the starting material.

In still another embodiment of the present invention, the protein hydrolysate does not impart any undesirable flavor to the finished product.

In yet another embodiment of the present invention, the solubility of the protein hydrolysate is independent of the pH value.

The process involves following process steps:
Defatted Soy Flour
Soybean flour is derived from clean round beans. The cleaned beans pass through a cracking process and the bean fragments are the graded on sieves and an aspirate system. The cleaned cracked meat is passed through a conditioner cooker and flaked. This is subjected to a solvent extraction process. The extracted flakes were desolventized and ground to 100 mesh. The specification for soy flour consists of (a) Moisture=9% by mass (max); (b) Protein on dry basis=48% by mass (min); (c) The total ash on dry basis=7.2% by mass (max); (d) Acid insoluble ash on dry basis=0.4% by mass (max); (e) Fat on dry basis=1.5% by mass; (f) Crude fibre on dry basis=4.2% by mass (max); (g) Aflatoxin=30 ppb (max); (h) Residual solvent=170 ppm; (I) Total bacterial count per gram=50,000; (j) Coliform bacteria/g=10; and (k) Salmonella bacterial=Nil.

Papain

The specification of the plant thiol protease papain is to obtain commercially available food grade enzyme having proteolytic activity not less than 2,000 tyrosine units (TU)/mg proteolytic activity.

Measurement of Degree of Hydrolysis

Trinitrobenzenesulphonic acid (TNBS) procedure is an accurate, reproducible and generally applicable procedure for determining the degree of hydrolysis of food protein hydrolysates. The protein is dissolved/dispersed in hot 1% sodium dodecyl suplphate to a concentration of 0.25–2.5× $10^{-3}$ aminoequivalents/L. A sample solution (0.25 ml) is mixed with 2 ml of 0.2125 M sodium phosphate buffer (pH 8.2) and 2 ml of 0.1% Trinitrobenzenesulphonic acid, followed by incubation in the dark for 60 min at 50 C. The reaction is quenched by adding 4 ml. of 0.10 N hydrochloric acid (HCl) and the absorbance is read at 340 nm. A 1.5 mM L-leucine solution is used as the standard. Transformation of the measured leucine amino equivalents to a degree of hydrolysis is carried out by means of a standard curve for each particular protein substrate (Adler Nissen, J. [1979] J. Agri. Food Chem. 27,6, 1256–1262).

Defatted soy bean flour was dispersed in water with a suitable solvent to solute ratio and the pH of the dispersion was adjusted using 6N sodium hydroxide or 6N hydrochloric acid. This was kept stirring for a few minutes with mechanical stirrer and the temperature raised to 50–55° C. At this stage 0.4–0.6 (w %) of papain on the basis of soy flour was added and stirring continued for 3–4 hours. At the end of the above time interval the temperature of the slurry was raised to 90–95° C. for 5–10 minutes. The slurry was cooled to room temperature and the insoluble carbohydrate-rich fraction in the dispersion was removed by centrifugation. The clarified protein hydrolysate was spray dried to obtain protein hydrolysate.

The following examples are given by way of illustrations of the present invention and should not be construed to limit the scope of the present invention.

EXAMPLE 1

100 g of defatted soy flour is dispersed in 500 ml of water and the pH of the dispersion was adjusted to 5.5 using 1N HCl. The solution stirred with mechanical stirrer and then the temperature raised to 50° C. by heating the solution. 500 mg of papain was added and stirring continued for 3 hrs. The enzyme was inactivated by boiling for 5 min. The pH of the hydrolysate was adjusted to 6.8 using 6N NaOH. The slurry was cooled and centrifuged. The clear solution was spray dried. The yield was 24% (on flour basis) and degree of hydrolysis was 30%.

EXAMPLE 2

300 g of deffated soy flour is dispersed in 1500 ml of water and the pH of the dispersion was adjusted to 5.5 using 1N HCl. The solution was stirred with mechanical stirrer and the temperature raised to 55° C. 1.5 g of papain was added and stirring continued for 3 h. The enzyme was inactivated by boiling for 5 min. The pH of the hydrolsate was adjusted to 6.8 using 6N NaOH. The slurry was cooled and centrifuged. The clear solution was spray dried. The yeild was 21% (on flour basis) and degree of hydrolysis was 30%.

EXAMPLE 3

1 kg of defatted soy flour was dispersed in 5000 ml of water and the pH of the dispersion was adjusted to 5.0 using 1N HCl. The solution stirred with mechanical stirrer and then the temperature raised to 50° C. 5 g of papain was added and stirring continued for 4 hrs. The enzyme was inactivated by boiling for 5 min. The pH of the hydroslate as adjusted to 6.5 using 6N NaOH. The slurry was cooled and centrifuged. The clear solution was spray dried. The yield was 20% (on flour basis) and degree of hydrolysis was 30%.

The particle size of the soy flour, ratio of enzyme to substrate, temperature, pH and time interval controls the end of enzymatic hydrolysis resulting in minimal bitterness of the hydrolysate.

The soya protein hydrolysate obtained has a creamy colour and a yield of 20–25% (on the basis of the flour). The product has 3.0–5.0% moisture, 8.0–8.5% nitrogen and 30.0–35.0% degree of hydrolysis (TNBS procedure).

The soy protein hydrolysate obtained has 25–30 trypsin inhibitor Unit/mg (TIU/mg) activity, 95–98% nitrogen solubility index, 1.0–1.4% of salt content (measured as CL ions) and 2–2.2 g/100 ml bitterness recognition threshold units. The lipoxygenase and urease activities were not detectable. The amino acid composition of the soy protein hydrolysate obtain was similar to the amino acid make-up of the starting raw material thereby retaining the nutritional value. The protein hydrolysate is less bitter compared to protein hydrolysate obtained from casein and is less hygroscopic in nature.

The main advantages of this invention are:
1. The enzyme employed is a food grade commercially-available acceptable plant enzyme with broad specificity resulting in 30–35% degree of hydrolysis.
2. The product can be a good additive without imparting any undesirable flavour to the finished product.
3. The hydrolysate has a solubility which is independent of pH making it a suitable additive either in acid pH or alkaline pH.
4. The final product is in the dry form suitable for different food formulations and is easy to handle.

What is claimed is:
1. A process for the preparation of a protein hydrolysate from soy flour, said process consisting of the steps of
   a. hydrolyzing an aqueous slurry of defatted soy flour containing 6–30% solid content w/v with a proteolytic enzyme of plant origin at pH 5–9 and at a temperature of 53+5° C. under stirring for a range of from 30 minutes to 6 hours;
   b. inactivating the enzyme by heating to 95–100° C. in a boiling water bath for 10 minutes;
   c. neutralizing the pH value of the slurry; and
   d. separating solids by centrifugation and drying the resultant clarified liquor to obtain said hydrolysate.
2. A process as claimed in claim 1, wherein the solid content of the slurry is 20% w/v.
3. A process as claimed in claim 1, wherein the plant origin proteolytic enzyme is added to the soy flour.

4. A process as claimed in claim 1, wherein 0.4–0.6% w/w of the proteolytic enzyme is added to the soy flour.

5. A process as claimed in claim 1, wherein the hydrolysis is effected for a period of 3–4 hours.

6. A process as claimed in claim 1, wherein the drying is effected by freeze drying, spray drying, or drum drying.

7. A process as claimed in claim 1, wherein the protein hydrolysate has 2–2.2 g/100 ml bitterness recognition threshold units.

8. A process as claimed in claim 1, wherein the protein hydrolysate obtained in step (4) has 30 to 35% degree of hydrolysis, as determined by Trinitrobenzenesulphonic acid (TNBS) procedure.

9. A process as claimed in claim 1, wherein the protein hydrolysate obtained has a color of cream and a yield of 20–25% on flour basis.

10. A process as claimed in claim 1, wherein protein hydrolysate has 3.0 to 5.0% moisture, 8.0 to 8.5% nitrogen, and 30.0–35.0% degree of hydrolysis, as determined by Trinitrobenzenesulphonic acid (TNBS) procedure.

11. A process as claimed in claim 1, wherein the protein hydrolysate obtained has 25–30 trypsin inhibitor units/mg activity, 95 to 98% Nitrogen Solubility Index and 1.0 to 1.4% of salt content.

12. A process as claimed in claim 1, wherein lipoxygenase and urease activities of the protein hydrolysate are not detectable.

* * * * *